US011635854B2

(12) United States Patent
Chi et al.

(10) Patent No.: US 11,635,854 B2
(45) Date of Patent: Apr. 25, 2023

(54) TOUCH SCREEN

(71) Applicant: BENQ CORPORATION, Taipei (TW)

(72) Inventors: Chin-Jui Chi, Taoyuan (TW); Pei-Wen Huang, Taoyuan (TW); Ta-Wei Liu, Taoyuan (TW)

(73) Assignee: BenQ Corporation, Taipei (TW)

( * ) Notice: Subject to any disclaimer, the term of this patent is extended or adjusted under 35 U.S.C. 154(b) by 0 days.

(21) Appl. No.: 17/686,511

(22) Filed: Mar. 4, 2022

(65) Prior Publication Data
US 2022/0305157 A1 Sep. 29, 2022

(30) Foreign Application Priority Data
Mar. 29, 2021 (TW) .................................. 110111268

(51) Int. Cl.
*G06F 3/042* (2006.01)
*A61L 2/10* (2006.01)
*G06F 3/041* (2006.01)
*A61L 2/26* (2006.01)

(52) U.S. Cl.
CPC ................ *G06F 3/042* (2013.01); *A61L 2/10* (2013.01); *A61L 2/26* (2013.01); *G06F 3/0412* (2013.01); *G06F 3/0421* (2013.01); *A61L 2202/11* (2013.01); *A61L 2202/14* (2013.01); *G06F 2203/04108* (2013.01)

(58) Field of Classification Search
CPC ......... G06F 3/042–0423; G06F 3/0428; G06F 3/041–047; G06F 2203/041–04114; G06F 3/0412
See application file for complete search history.

(56) References Cited

U.S. PATENT DOCUMENTS

2011/0256019 A1* 10/2011 Gruen ........................ A61L 2/10
345/173
2021/0052756 A1* 2/2021 Kim ..................... F21V 33/0052

OTHER PUBLICATIONS

Office action of counterpart application by Taiwan IP Office dated Jan. 25, 2022.

* cited by examiner

*Primary Examiner* — Sanjiv D. Patel

(57) ABSTRACT

A touch display screen includes a display panel, a touch-sensing part, a biosensor and a controller. The touch-sensing part is disposed on a light emitting side of the display panel and has a touch-sensing surface. The touch-sensing part includes a light-emitting device and a light receiver. The light-emitting device is used to provide at least one positioning light and at least one high-energy light. The light receiver is used to detect a change of the positioning light on the touch-sensing surface in response to a touch action and determine the position on which the touch action occurs on the touch-sensing surface. The biosensor is used to determine whether a living body getting close to the touch-sensing surface. The controller is used to drive the light-emitting device to selectively provide the positioning light and/or the high-energy light to the touch-sensing surface according to the determinations of the biosensor.

16 Claims, 3 Drawing Sheets

TOUCH SCREEN

This application claims the benefit of Taiwan application Serial No. 110111268, filed Mar. 29, 2021, the subject matter of which is incorporated herein by reference.

BACKGROUND

Technical Field

The disclosure relates to a touch screen, and more particularly, to a touch screen with sterilization function.

Description of Background

With the development of today's technology, electronic products have become an indispensable part of people's lives. Particularly to the electronic products with touch screens, such as tablet computers, smart phones and smart watches, may become more and more popular.

However, when operating the electronic products, since the user needs to continuously touch the touch screen with fingers, or repeatedly slide the fingers on the touch screen, thus it may easily cause personal hygiene problems due to bacteria or virus growth and accumulation on the touch screen.

Therefore, there is a need of providing a touch screen to obviate the drawbacks encountered from the prior art.

SUMMARY

One aspect of the present disclosure is to provide a touch screen, wherein the touch screen includes a display panel, a touch-sensing part, a biosensor and a controller. The touch-sensing part is disposed on a light emitting side of the display panel and has a touch-sensing surface. The touch-sensing part includes a light-emitting device and a light receiver. The light-emitting device is used to provide at least one positioning light and at least one high-energy light. The light receiver is used to detect a change of the positioning light on the touch-sensing surface in response to a touch action and determine the position on which the touch action occurs on the touch-sensing surface. The biosensor is used to determine whether there is a living body getting close to the touch-sensing surface. The controller is used to drive the light-emitting device to selectively provide the positioning light and/or the high-energy light to the touch-sensing surface according to the determinations of the biosensor.

In accordance with the aforementioned embodiments of the present disclosure, a touch screen including a display panel, a touch-sensing part with an optical touch panel, a biosensor and a controller is provided. The touch-sensing part includes a light-emitting device that can provide lights of two or more different wavelengths. Wherein, the light with longer wavelength can be used as the positioning lights of the optical touch panel; and the light with shorter wavelength and high-energy can be used to irradiate the touch-sensing surface of the optical touch panel to provide a sterilization function. The biosensor can determine whether there is a living body getting close to the touch-sensing surface, and then the controller selectively turns on/off the light-emitting units in the light-emitting device (or modulates the voltage/current applied to the light-emitting units in the light-emitting device) according to the determination of the biosensor, so as to provide the positioning light and/or high-energy light required to the touch-sensing surface of the optical touch panel at the appropriate position and time. Such that, the user can be prevented from being negatively affected by the high-energy (such as an ultraviolet light), while providing the sterilization function to the display panel; and the power consumption of the touch screen can be saved when the user performs the touch operation.

BRIEF DESCRIPTION OF THE DRAWINGS

The above objects and advantages of the present disclosure will become more readily apparent to those ordinarily skilled in the art after reviewing the following detailed description and accompanying drawings, in which.

DETAILED DESCRIPTION

Figure 1:
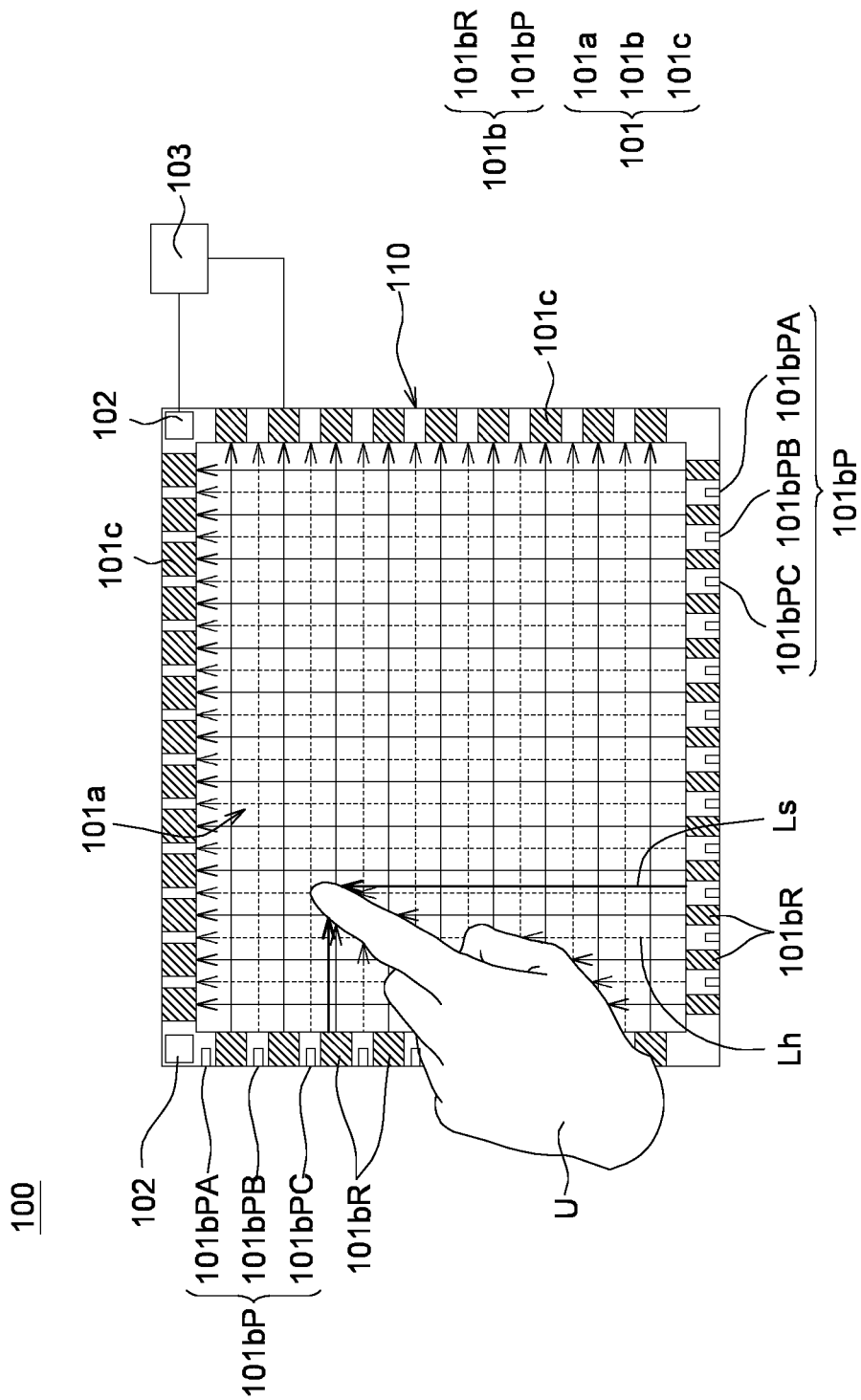
FIG. 1 is a top view illustrating the structure of a touch screen, according to one embodiment of the present disclosure.

The embodiments as illustrated below provide a touch screen to provide sterilization function to a touch panel while preventing a user from being negatively affected by the high-energy light of the sterilization when performing a touch operation, and to save the power consumption of the touch screen. The present disclosure will now be described more specifically with reference to the following embodiments illustrating the structure and arrangements thereof.

It is to be noted that the following descriptions of preferred embodiments of this disclosure are presented herein for purpose of illustration and description only. It is not intended to be exhaustive or to be limited to the precise form disclosed. Also, it is important to point out that there may be other features, elements, steps, and parameters for implementing the embodiments of the present disclosure which are not specifically illustrated. Thus, the descriptions and the drawings are to be regard as an illustrative sense rather than a restrictive sense. Various modifications and similar arrangements may be provided by the persons skilled in the art within the spirit and scope of the present disclosure. In addition, the illustrations may not be necessarily drawn to scale, and the identical elements of the embodiments are designated with the same reference numerals.

FIG. 1 is a top view illustrating the structure of a touch screen 100, according to one embodiment of the present disclosure. The touch screen 100 includes a display panel 110, a touch-sensing part 101, a biosensor 102 and a controller 103.

In some embodiments of the present disclosure, the display panel 110 may be a liquid crystal display (LCD) panel, an organic light-emitting diode (OLED) panel, a micro light-emitting diode (Micro-LED) panel, an electronic paper display (EPD) panel or an electronic ink (E-Ink) display panel. In the present embodiment, the display panel 110 can be a LCD panel built in a mobile phone. However, the display panel 110 is not limited thereto, any form and type of display screen or display medium used to display images and built in any electronic product does not depart from the spirit of the display panel 110 described in the present disclosure. For example, in another embodiment, the display panel 110 may be a large-scale display panel used for a billboard fixed or movable indoor or outdoor.

The touch-sensing part 101 is disposed on the light-emitting side 110a of the display panel 110 on which images displayed. The touch-sensing part 101 may be an optical touch panel, having a touch-sensing surface 101a, at least one light-emitting device 101b and at least one light receiver 101c. The light-emitting device 101b is used for providing at least one positioning light Ls and at least one high-energy light Lh. Wherein, the wavelength of the positioning light Ls is substantially greater than the wavelength of the high-energy light Lh. The light receiver 101c is used to detect the light change generated by the positioning light Ls (or the high-energy light Lh, or the combination of these two) on the touch-sensing surface 101a in response to the touch action performed by a user U or resulted from other objects, so as to determine the touch point P of the user U (or the other objects) on which the touch action occurs on the touch-sensing surface 101a.

For example, in some embodiments of the present disclosure, the touch-sensing part 101 may be an optical touch panel using laser projection technology. Wherein, the light-emitting device 101b disposed on one side (eg, the left side and the lower side) of the touch-sensing surface 101a is utilized to provide a plurality of laser beams serving as the positioning light Ls; and the light receiver 101c disposed on the corresponding side (eg, the right side and the upper side) of the touch-sensing surface 101a is used to receive the positioning light Ls correspondingly. When the user U or the other objects touch the position P on the touch-sensing surface 101a, part of the positioning light Ls originally passed through the position P can be blocked, scattered, absorbed or interfered, so that the signal of the positioning light Ls received by the light receiver 101c (e.g., optical density, optical spectrum, or the combination of these two) may change in magnitude, thereby the coordinates of the position P on the touch-sensing surface 101a can be determined by figuring out to the location on which the signal change occurs.

In the present embodiment, the light-emitting device 101b may include at least one first light source, such as a plurality of infrared light-emitting units 101bR, arranged on one side (e.g., the left side and the lower side) of the touch-sensing surface 101a to provide a plurality of infrared light beams (with wavelengths between 760 nm to 1 millimeter (mm)) serving as the positioning light Ls, and form a light grid pattern on the touch-sensing surface 101a. When the user U touches the position P on the touch-sensing surface 101a, a part of the positioning light Ls that originally passed through the position P may be blocked or all of the positioning light Ls may be blocked, so that the corresponding light receiver 101c does not receive the signal of the blocked part of the positioning light Ls, or the overall light density measured by the light receiver 101c may be changed in magnitude, thereby the coordinates of the position P can be determined by the light grid pattern formed on the touch-sensing surface 101a. And the changes of the light density or the coordinates of the position P can be notified to the controller 103 of in real time.

In some embodiments of the present disclosure, the wavelengths of the infrared light beams (the positioning lights Ls) emitted by the infrared light emitting units 101bR may be the same or different. In the present embodiment, the infrared light emitting units 101bR emit infrared beams (the positioning lights Ls) with the same wavelength, and preferably the wavelength of the positioning lights Ls is about 850 nm.

In addition, the light-emitting device 101b further includes at least one second light source capable of providing high-energy light Lh, such as a plurality of ultraviolet light-emitting units 101bP, staggered with the plurality of infrared light-emitting units 101bR and capable of emitting a plurality of ultraviolet light rays (i.e., high-energy lights Lh) having wavelengths ranging from 10 nm to 400 nm, that can be used to irradiate the touch-sensing surface 101a of the touch-sensing part 101 for providing a sterilization function. In some embodiments of the present disclosure, a layer of photocatalyst film (not shown) may also be disposed on the touch-sensing surface 101a of the touch-sensing part 101. When the ultraviolet rays (i.e., the high-energy lights Lh) irradiates the photocatalyst film, the photocatalyst film can be triggered to generate a radiation to sterilize the touch-sensing surface 101a of the touch-sensing part 101.

The ultraviolet rays (i.e., the high-energy lights Lh) emitted by the ultraviolet light-emitting units 101bP may have the same wavelength or different wavelengths. In the present embodiment, the ultraviolet light-emitting units 101bP (the second light sources) may include at least one long-wavelength ultraviolet light-emitting element 101bPA capable of emitting long-wavelength ultraviolet rays (UVA) having wavelengths ranging from 320 nm and 400 nm, at least one mid-wavelength ultraviolet light-emitting element 101bPB capable of emitting mid-wavelength ultraviolet rays (UVB) ranging from 280 nm and 320 nm and at least one short-wavelength ultraviolet light emitting element 101bPC capable of emitting short-wavelength ultraviolet rays (UVC) having wavelengths ranging from 100 nm and 280 nm.

It should be appreciated that, although FIG. 1A only depicts that a plurality of ultraviolet light-emitting units 101bP and a plurality of infrared light-emitting units 101bR of the light-emitting device 101b are respectively staggered on one side of the touch-sensing surface 101a, but the arrangement of the ultraviolet light-emitting units 101bP and the infrared light-emitting units 101bR are not limited to this regard. For example, in some embodiments, the ultraviolet light-emitting units 101bP and the infrared light-emitting units 101bR can be firstly integrated on the same substrate (not shown) to form a sub-light-emitting assembly (not shown), and then arrange the sub-light-emitting assembly on one side of the touch-sensing surface 101a according to different design requirements.

The biosensor 102 can be built in the control circuit of the display panel 110, or can be set up separately outside the display panel 110, and is electrically connected to the touch touch-sensing part 101 and the controller 103 to determine whether there is a living body (eg, user U) getting close to the touch-sensing surface 101a. The operation of the biosensor 102 is measuring the physical quantity changes at a position (not shown) separated from the touch-sensing surface 101a for a predetermined safe distance along a normal vector (not shown) perpendicular to the touch-sensing surface 101a to determine whether there is a living body (e.g., the user U) getting close to the touch-sensing surface 101a.

For example, in one embodiment of the present disclosure, the biosensor 102 can be a proximity sensor that can emit an electromagnetic field or electromagnetic radiation (e.g., an infrared beam), receive the reflected signal thereof, and compare the change of the emitted electromagnetic field/radiation and the reflected signal for a certain time under the conditions of contacting or not contacting a foreign living body (e.g., the user U), to determine whether there is a living body getting close to the touch-sensing surface 101a.

In another embodiment of the present disclosure, the biosensor 102 can be a photometric sensor, which can determine whether there is a living body getting close to the touch-sensing surface 101a by sensing the photometric change at a position (not shown) separated from the touch-sensing surface 101a for a predetermined safe distance. In yet another embodiment of the present disclosure, the biosensor 102 can be a temperature sensor, which can determine whether there is a living body getting close to the touch-sensing surface 101a by sensing the temperature change at a position (not shown) separated from the touch-sensing surface 101a for a predetermined safe distance. In yet another embodiment of the present disclosure, the biosensor 102 can be an image recognizer, which can determine whether there is a living body getting close to the touch-sensing surface 101a by capturing image data in front of the touch-sensing surface 101a, and performing image comparison and analysis. In yet another embodiment of the present disclosure, the biosensor 102 can be an audio sensor, which can determine whether there is a living body getting close to the touch-sensing surface 101a by sensing the sound change at a position (not shown) separated from the touch-sensing surface 101a for a predetermined safe distance.

However, it should be noted that the types of the biosensor 102 and sensing methods applied by the biosensor 102 are not limited thereto, and various types and sensing methods can be mixed and matched. In addition, the position of the biosensor 102 is not specific. For example, in some embodiments, the biosensor 102 may be disposed at any position on the light-emitting side 110a of the display panel 110. In the present embodiment, the biosensor 102 is disposed on the touch-sensing surface 101a of the touch-sensing part 101. In other embodiments, the biosensor 102 may be disposed separately from the display panel 110.

The controller 103 can be built in the control circuit of the display panel 110, or can be separately set up outside the display panel 110, and is electrically connected to the biosensor 102, or further electrically connected to the touch-sensing part 101. The controller 103 can drive the light-emitting device 101b to selectively provide the positioning light Ls and/or high-energy light Lh to the touch-sensing surface 101a according to the determination of the biosensor 102.

For example, in the present embodiment, the high-energy light Lh used for sterilization of the touch-sensing surface 101a may cause potential damage to the skin or eyes of the user U. Therefore, when the biosensor 102 determines that there is a living body getting close to the touch-sensing surface 101a, the controller 103 can drive the light-emitting device 101b to only turn on the plurality of infrared light-emitting units 101bR (the first light sources) according to the determination of the biosensor 102, and turn off the ultraviolet light-emitting unit 101bP (second light source). Such that, when the user U operates the touch screen 100, the touch function of the touch-sensing part 101 can operate normally, while preventing the ultraviolet rays (i.e., high-energy lights Lh) emitted by the ultraviolet light-emitting unit 101bP (the second light source) from directly irradiating to the user U.

Conversely, when the biosensor 102 determines that no living body getting close to the touch-sensing surface 101a, the controller 103 can drive the light-emitting device 101b to only turn on the ultraviolet light-emitting units 101bP (the second light source) and turn off the infrared light emitting units 101bR (first light sources) according to the determination of the biosensor 102. Whereby the ultraviolet light-emitting units 101bP can emit ultraviolet rays to irradiate the touch-sensing surface 101b and sterilize the touch-sensing part 101; and the power of the touch screen 100 can be save by turning off the light-emitting units 101bP.

In the present embodiment, the controller 103 can selectively turn on/off the ultraviolet light-emitting elements 101bPA, 101bPB and 101bPC, and modulate the switching time of the ultraviolet light-emitting elements 101bPA, 101bPB and 101bPC respectively, according to the determination of the biosensor 102 and considering the time intervals of which no living body getting close to the touch-sensing surface 101a.

However, the way of which the controller 103 selectively providing the positioning light Ls and/or the high-energy light Lh to the touch-sensing surface 101a is not limited thereto. In other embodiments, the controller 103 can selectively only turn off or turn on a part of the infrared light emitting units 101bR (the first light source) or only turn off or turn on a part of the ultraviolet light emitting units 101bP (the second light source) according to the determination of the biosensor 102. In some other embodiments, the controller 103 may change the wavelength of the positioning light Ls by controlling the voltage applied to the infrared light emitting units 101bR (the first light source) according to a predetermined setting; or change the brightness of the positioning light Ls by controlling the amount of current passing through the infrared light-emitting units 101bR.

Figure 2:
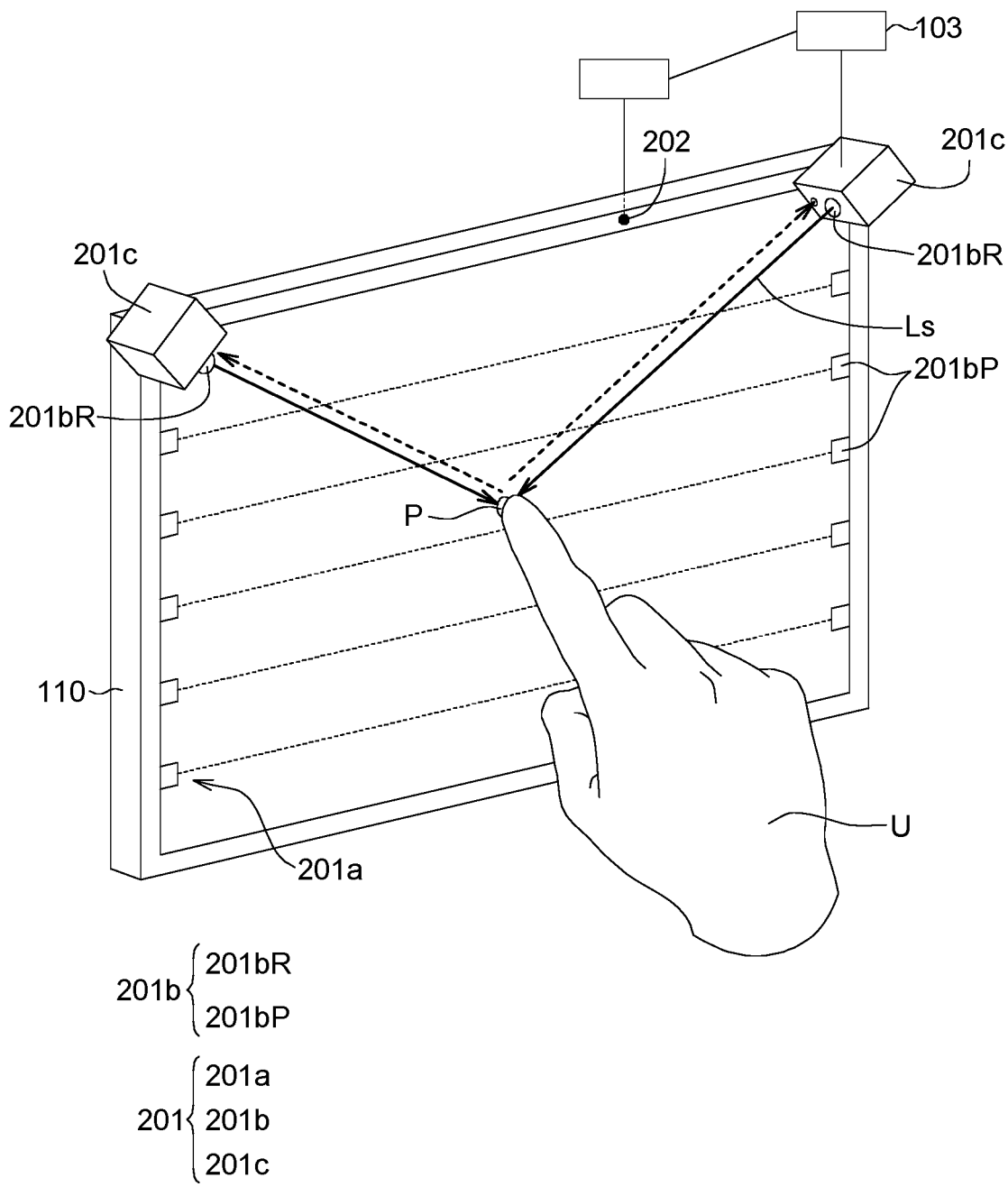
FIG. 2 is a cross-sectional view illustrating the structure of a touch screen, according to another embodiment of the present disclosure.

FIG. 2 is a cross-sectional view illustrating the structure of a touch screen 200, according to another embodiment of the present disclosure. The structure of the touch screen 200 is similar to that of the touch screen 100 as depicted in FIG. 1; and the main difference lies in the touch-sensing part 201 of the touch screen 200. In the present embodiment, the touch-sensing d device 201 used in the touch screen 200 is an optical imaging touch (OIT) device.

The touch-sensing part 201 includes at least one infrared light-emitting unit 201bR (the first light source), at least one ultraviolet light-emitting unit 201bP (the second light source) and at least one infrared camera (IR camera) 201c all disposed around the touch-sensing surface 201a. When the user U or other objects getting close to or touch the position P of the touch-sensing surface 201a, a shadow that blocks infrared rays can be generated at the position P. At this time, the IR camera 201c can use the image sensing element (such as photodiode, charge-coupled device (CCD) or Intensified CCD (ICCD)), serving as a light receiver, to capture information (such as the orientation, width, height, and cusp) of the shadow to determine the coordinates of the position P on the touch-sensing surface 201a, so as to achieve the touch-sensing function.

The ultraviolet light-emitting unit 201bP (the second light source) can emit ultraviolet rays with a wavelength ranging from 100 nm to 400 nm, referring to as the high-energy light Lh, irradiating the touch-sensing surface 201a of the touch-sensing part 201 to provide the function of sterilization. Since the touch display screens 200 and 100 both use the same biosensor 202 and the controller 203 to control the infrared light-emitting unit 201bR (the first light source) and the ultraviolet light-emitting unit 201bP (the second light source), and the regulation and control methods of these two are similar, thus they are not redundantly repeated here.

Figure 3:
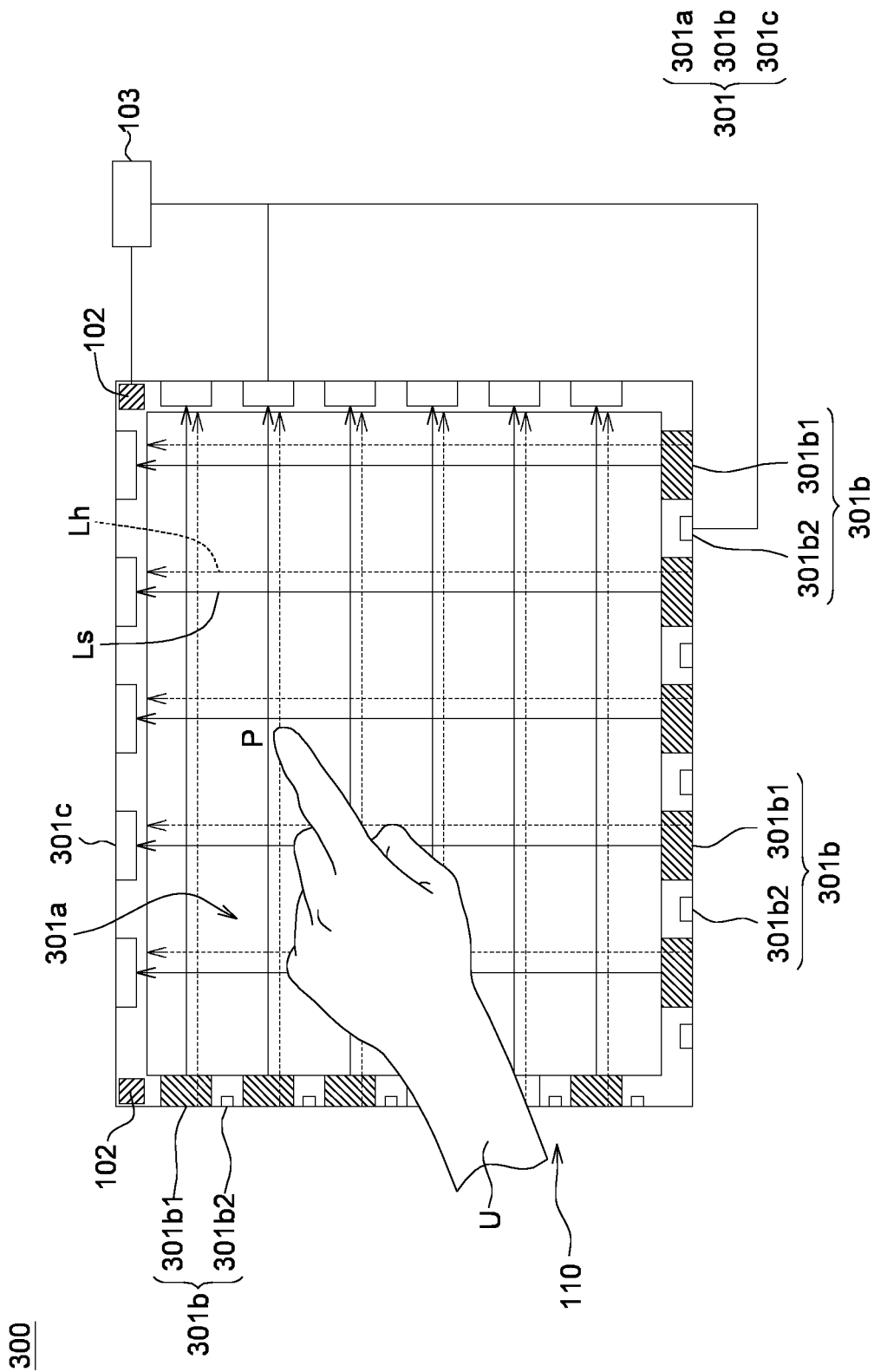
FIG. 3 is a top view illustrating the structure of a touch screen, according to yet another embodiment of the present disclosure.

FIG. 3 is a top view illustrating the structure of a touch screen 300, according to yet another embodiment of the present disclosure. The structure of the touch screen 300 is similar to that of the touch screen 100 as depicted in FIG. 1; and the main difference lies in the structure and control method of the light-emitting device 301b in the touch-sensing part 301. In the present embodiment, the touch-sensing part 301 has a touch-sensing surface 301a, and includes a plurality of light-emitting devices 301b and a plurality of light receivers 301c.

A plurality of light-emitting devices 301b are arranged on at least one side (e.g., the left side and the lower side) of the touch-sensing surface 301a, and a plurality of light receivers 301c are disposed on another side (e.g., the right side and the upper side) of the touch-sensing surface 301a corresponding to the plurality of light-emitting devices 301b, for correspondingly receiving the light emitted by the light-emitting devices 301b. Each of the light-emitting devices 301b includes a plurality of electroluminescent units 301b1 and a wavelength modulator 301b2. The wavelength of the light emitted by the electroluminescent unit 301b1 can be modulated in different ways. The modulator 301b2 is used for modulating the wavelength of the light emitted by the electroluminescent unit 301b1, so as to provide at least one positioning light Ls or at least one high-energy light Lh.

For example, in the present embodiment, each electroluminescent unit 301b1 may be an electroluminescent unit include material of aluminum gallium arsenide (AlGaAs), gallium nitride (GaN), indium gallium nitride (InGaN), aluminum indium gallium nitride (AlN), Indium Gallium Nitride (AlGaN) or a composite material formed by any combination of the above. The wavelength modulator 301b2 includes a voltage/current modulator for responding to a control signal provided by the controller 303 to modulate the input power applied to each of the electroluminescence units 301b1, so that he output wavelength of the electroluminescence units 301b1 can changed in response to the change of the input power.

When the biosensor 102 determines that there is a living body getting close to the touch-sensing surface 301a, the controller 303 can modulate the input power applied to each electroluminescence unit 301b1 according to the determination of the biosensor 102, so as to make the electroluminescent units 301b1 emitting infrared light with a wavelength substantially ranging from 760 nm to 1 mm (serving as the positioning light Ls) according to the input power. When the user U or other objects touch the position P on the touch-sensing surface 301a, the part of the positioning light Ls originally passed through the position P can be blocked, so that the corresponding light receiver 301c cannot receive the blocked positioning light Ls (or can measure the change of the optical density of the positioning light Ls), thereby the coordinates of the position P can be determined on the touch-sensing surface 301a, so as to provide the touch-sensing function of the touch screen 300.

When the biosensor 102 determines that there is no living body getting close to the touch-sensing surface 101a, the controller 303 can adjust the input power applied to each electroluminescence unit 301b1 according to the determination of the biosensor 102, so as to make the electroluminescent units 301b1 emitting ultraviolet rays (serving as the high-energy light Lh for performing sterilization) with a wavelength substantially ranging from 100 nm to 400 nm in response to the input power to irradiate the touch-sensing surface 301a of the touch-sensing part 301.

In some embodiments of the present disclosure, the controller 303 may selectively modulate the input power applied to each of the electroluminescent units 301b1 according to the time interval of which no living body getting close to the touch-sensing surface 301a, so that the electroluminescent units 301b1 can emit ultraviolet rays with different wavelengths, such as UVA, UVB or UVC, according to the input power.

In accordance with the aforementioned embodiments of the present disclosure, a touch screen including a display panel, a touch-sensing part with an optical touch panel, a biosensor and a controller is provided. The touch-sensing part includes a light-emitting device that can provide lights of two or more different wavelengths. Wherein, the light with longer wavelength can be used as the positioning lights of the optical touch panel; and the light with shorter wavelength and high-energy can be used to irradiate the touch-sensing surface of the optical touch panel to provide a sterilization function. The biosensor can determine whether there is a living body getting close to the touch-sensing surface, and then the controller selectively turns on/off the light-emitting units in the light-emitting device (or modulates the voltage/current applied to the light-emitting units in the light-emitting device) according to the determination of the biosensor, so as to provide the positioning light and/or high-energy light required to the touch-sensing surface of the optical touch panel at the appropriate position and time. Such that, the user can be prevented from being negatively affected by the high-energy (such as an ultraviolet light), while providing the sterilization function to the display panel; and the power consumption of the touch screen can be saved when the user performs the touch operation.

While the disclosure has been described by way of example and in terms of the exemplary embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A touch screen, comprising:
    a display panel,
    a touch-sensing part, disposed on a light emitting side of the display panel, having a touch-sensing surface and comprising:
        a light-emitting device, used to provide at least one positioning light and at least one high-energy light; and
        a light receiver, used to detect a change of the positioning light on the touch-sensing surface in response to a touch action and determine a position on which the touch action occurs on the touch-sensing surface;
    a biosensor, used to determine whether there is a living body getting close to the touch-sensing surface; and
    a controller, used to drive the light-emitting device to selectively provide the positioning light and/or the high-energy light to the touch-sensing surface according to determinations of the biosensor;
    wherein the light-emitting device further comprises a wavelength modulator driven by the controller according to the determination of the biosensor and considering time intervals of which the living body not getting close to the touch-sensing surface.

2. The touch screen according to claim 1, wherein the light-emitting device comprises:
    a first light source, for providing the at least one positioning light; and
    a second light source, for providing the at least one high-energy light.

3. The touch screen according to claim 2, wherein the light-emitting device further comprises a switch element connected to the first light source and the second light source, and driven by the controller to turn on/off the first light source and the second light source according to the determinations of the biosensor.

4. The touch screen according to claim 1, wherein the light-emitting device comprises:
    a light source; and the wavelength modulator is used for modulating an output wavelength of the light source to provide the at least one positioning light and the at least one high-energy light.

5. The touch screen according to claim 4, wherein the wavelength modulator comprises a voltage/current modulator driven by the controller to modulate an input power applied to the light source for changing the output wavelength of the light source.

6. The touch screen according to claim 1, wherein the biosensor measures a physical quantity change at a position separated from the touch-sensing surface for a predetermined safe distance along a normal vector perpendicular to the touch-sensing surface to determine whether there is a living body getting close to the touch-sensing surface.

7. The touch screen according to claim 1, wherein the biosensor is selected from a group consisting of a proximity sensor, a photometric sensor, a temperature sensor, an image recognizer, an audio sensor and arbitrary combinations thereof.

8. The touch screen according to claim 1, wherein the at least one positioning light has a wavelength greater than that of the at least one high-energy light.

9. The touch screen according to claim 1, wherein the at least one high-energy light has a wavelength ranging from 100 nm to 400 nm.

10. The touch screen according to claim 1, wherein
when the biosensor determines that the living body is getting close to the touch-sensing surface, the controller drives the light-emitting device providing the at least one positioning light to the touch-sensing surface, and stopping to provide the at least one high-energy light to the touch-sensing surface;
when the biosensor determines that the living body is not getting close to the touch-sensing surface, the controller drives the light-emitting device providing the at least one high-energy light to the touch-sensing surface.

11. The touch screen according to claim 2, wherein the controller changes a wavelength of the at least one positioning light by controlling the voltage applied to the first light source, and changes a brightness of the at least one positioning light by controlling a current passing through the first light source.

12. The touch screen according to claim 10, wherein when the biosensor determines that the living body is departing from the touch-sensing surface, the controller drives the light-emitting device stopping to provide the at least one positioning light.

13. The touch screen according to claim 1, wherein the at least one high-energy light is a long-wavelength ultraviolet ray (UVA), a mid-wavelength ultraviolet ray (UVB), a short-wavelength ultraviolet ray (UVC) or arbitrary combinations thereof.

14. The touch screen according to claim 1, wherein the at least one positioning light is an infrared light with a wavelength ranging from 760 nm to 1 mm.

15. The touch screen according to claim 1, wherein the light-emitting device comprises a plurality of ultraviolet light-emitting units used to provide a plurality of high-energy lights with a plurality of wavelengths.

16. The touch screen according to claim 15, wherein the controller selectively turns on or off at least one of the plurality of ultraviolet light-emitting units according to the determination of the biosensor and considering time intervals of which the living body not getting close to the touch-sensing surface.

\* \* \* \* \*